(12) United States Patent
Hossainy

(10) Patent No.: US 8,202,530 B2
(45) Date of Patent: Jun. 19, 2012

(54) BIOCOMPATIBLE COATINGS FOR STENTS

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1895 days.

(21) Appl. No.: 11/288,754

(22) Filed: Nov. 28, 2005

(65) Prior Publication Data

US 2006/0078588 A1    Apr. 13, 2006

Related U.S. Application Data

(63) Continuation of application No. 10/260,182, filed on Sep. 27, 2002.

(51) Int. Cl.
*A61F 2/02* (2006.01)

(52) U.S. Cl. ........................................ 424/426

(58) Field of Classification Search ................ None
See application file for complete search history.

(56) References Cited

U.S. PATENT DOCUMENTS

| | | | |
|---|---|---|---|
| 4,977,901 A | 12/1990 | Ofstead | |
| 5,017,370 A | 5/1991 | Hunter et al. | |
| 5,112,457 A | 5/1992 | Marchant | |
| 5,328,471 A | 7/1994 | Slepian | |
| 5,455,040 A | 10/1995 | Marchant | |
| 5,464,650 A | 11/1995 | Berg et al. | |
| 5,578,073 A | 11/1996 | Haimovich et al. | |
| 5,605,696 A | 2/1997 | Eury et al. | |
| 5,667,767 A | 9/1997 | Greff et al. | |
| 5,670,558 A | 9/1997 | Onishi et al. | |
| 5,700,286 A | 12/1997 | Tartaglia et al. | |
| 5,716,981 A | 2/1998 | Hunter et al. | |
| 5,824,049 A | 10/1998 | Ragheb et al. | |
| 5,830,178 A | 11/1998 | Jones et al. | |
| 5,837,313 A | 11/1998 | Ding et al. | |
| 5,851,508 A | 12/1998 | Greff et al. | |
| 5,858,746 A | 1/1999 | Hubbell et al. | |
| 5,865,814 A | 2/1999 | Tuch | |
| 5,873,904 A | 2/1999 | Ragheb et al. | |
| 5,897,911 A * | 4/1999 | Loeffler | 427/2.25 |
| 5,971,954 A | 10/1999 | Conway et al. | |
| 5,980,928 A | 11/1999 | Terry | |
| 5,980,972 A | 11/1999 | Ding | |
| 5,994,341 A | 11/1999 | Hunter et al. | |
| 6,015,541 A | 1/2000 | Greff et al. | |
| 6,042,875 A | 3/2000 | Ding et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,113,629 A | 9/2000 | Ken | |
| 6,120,536 A | 9/2000 | Ding et al. | |
| 6,120,904 A | 9/2000 | Hostettler et al. | |
| 6,121,027 A | 9/2000 | Clapper et al. | |
| 6,129,761 A | 10/2000 | Hubbell | |
| 6,153,252 A | 11/2000 | Hossainy et al. | |
| 6,165,212 A | 12/2000 | Dereume et al. | |
| 6,663,880 B1 | 12/2003 | Roorda et al. | |
| 6,743,462 B1 | 6/2004 | Pacetti | |
| 2001/0008888 A1 | 7/2001 | Zenke et al. | |

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |

\* cited by examiner

*Primary Examiner* — Carlos Azpuru
(74) *Attorney, Agent, or Firm* — Squire Sanders (US) LLP

(57) ABSTRACT

A coating for a medical device, particularly for a stent, is described. The coating comprises a polymer and a biologically responsive compound. The coating can also contain a drug to provide enhanced therapeutic effect.

20 Claims, No Drawings

BIOCOMPATIBLE COATINGS FOR STENTS

CROSS-REFERENCE TO RELATED APPLICATIONS

This application is a continuation of U.S. application serial Ser. No. 10/260,182, filed Sep. 27, 2002.

BACKGROUND

1. Field of the Invention

The present invention relates to coatings for medical devices such as stents.

2. Description of the State of the Art

Stents act as scaffolding structures, functioning to physically hold open and, if desired, to expand the wall of the passageway. Typically stents are capable of being compressed, so that they can be inserted through small lumens via catheters, and then expanded to a larger diameter once they are at the desired location. Mechanical intervention via stents has reduced the rate of restenosis as compared to balloon angioplasty; restenosis, however, is still a significant clinical problem. Treating restenosis in stented vessels can be challenging, as clinical options are more limited as compared to lesions that were treated solely with a balloon.

In order to more effectively treat restenosis, stent implantation procedures are being supplemented with a pharmaceutical regimen. Systemic administration of drugs for the treatment of restenosis can produce adverse of toxic side effects for the patient. Local delivery is a preferred method of treatment in that smaller to total levels of medication are administered in comparison to systemic dosages, but are concentrated at a specific site. Local delivery thus produces fewer side effects and achieves more favorable results.

Being made of metal, stents need to be modified so as to provide a suitable means of locally delivering a drug. A polymeric coated stent has proved to be a very effective way of allowing a stent to systemically deliver a drug. A solution of a polymer dissolved in a solvent and a therapeutic substance added thereto is applied to the stent and the solvent is allowed to evaporate. Accordingly, a polymeric coating impregnated with a therapeutic substance remains on the surface of the stent.

To the extent that the mechanical functionality of stents has been optimized, continued improvements can be made to the coating of the stent. For example, the biocompatibility of the polymeric coating can be improved. The embodiments of the present invention provide different methods of enhancing the biocompatibility of polymeric coatings.

SUMMARY

According to one embodiment of the present invention, a coating for an implantable medical device is provided, the coating comprises at least one polymer and a biologically responsive component physically blended with the polymer, wherein the biologically responsive component is selected from a group consisting of a group consisting of PLURONIC® polyols, poly(vinyl pyrrolidone), hyaluronic acid, carboxymethylcellulose, poly(ethylene imine), poly(vinyl alcohol), polyacrylamide, sulfonated dextrane, silk-elastin block-copolymers, poly(ethylene oxide-co-ethylene imine), poly(ethylene oxide-co-vinyl pyrrolidone), poly(ethylene oxide-co-vinyl alcohol), poly(ethylene oxide-co-acrylamide), poly(ethylene oxide-co-sulfonated dextrane), PEG-hyaluronic acid adducts, adducts of silk-elastin block-copolymers with hyaluronic acid, sodium dodecyl sulfate, and blends thereof. The coating can additionally include poly(ethylene glycol) physically blended with the biologically responsive component.

According to another embodiment of the present invention, a method for inhibiting restenosis is provided, the method comprises delivering a restenosis-inhibiting substance to a treatment site, the substance physically blended into a polymeric coating applied on a medical device, wherein the restenosis-inhibiting substance is selected from a group consisting of PLURONIC polyols, poly(vinyl pyrrolidone), hyaluronic acid, carboxymethylcellulose, poly(ethylene imine), poly(vinyl alcohol), polyacrylamide, sulfonated dextrane, silk-elastin block-copolymers, poly(ethylene oxide-co-ethylene imine), poly(ethylene oxide-co-vinyl pyrrolidone), poly(ethylene oxide-co-vinyl alcohol), poly(ethylene oxide-co-acrylamide), poly(ethylene oxide-co-sulfonated dextrane), PEG-hyaluronic acid adducts, adducts of silk-elastin block-copolymers with hyaluronic acid, sodium dodecyl sulfate, and blends thereof.

According to yet another embodiment of the present invention, a method of coating a stent is provided, the method comprises applying a physical blend of a polymer and a biologically responsive component to the stent, wherein the biologically responsive component is selected from a group consisting of PLURONIC polyols, poly(vinyl pyrrolidone), hyaluronic acid, carboxymethylcellulose, poly(ethylene imine), poly(vinyl alcohol), polyacrylamide, sulfonated dextrane, silk-elastin block-copolymers, poly(ethylene oxide-co-ethylene imine), poly(ethylene oxide-co-vinyl pyrrolidone), poly(ethylene oxide-co-vinyl alcohol), poly(ethylene oxide-co-acrylamide), poly(ethylene oxide-co-sulfonated dextrane), PEG-hyaluronic acid adducts, adducts of silk-elastin block-copolymers with hyaluronic acid, sodium dodecyl sulfate, and blends thereof.

DETAILED DESCRIPTION

According to embodiments of the present invention, a stent coating can include the following polymeric layers: an optional primer layer, a drug-polymer (also referred to as "matrix layer" or "reservoir layer"), an optional topcoat layer ("topcoat"), and an optional finishing layer. At least one of the polymeric layers can contain a biologically responsive compound physically blended with the polymer forming the respective layer. The biologically responsive compound is non-fouling, non-immunogenic, and non-platelet activating. The term "non-fouling" refers to compounds which reduce or prevent deposits of proteins from forming on the outer surface of the stent coating. The term "non-immunogenic" refers to compounds which do not trigger the immune response of the body or reduce the immune response when the stent coating comes into contact with bodily fluids such as blood. At least one of the polymeric layers may also optionally contain a low molecular weight salt, for example, sodium chloride or potassium chloride.

The matrix layer can also optionally contain a biologically active substance (or drug). If a drug is used, the biologically responsive compound can also serve as a permeation enhancer, i.e., can facilitate the process of delivery of the drug to the diseased site.

Bodily fluids can slowly penetrate the coating and the biologically responsive compound can gradually dissolve in the body fluids and be carried to the diseased site. When the biologically responsive compound has arrived to the site to be treated, it can penetrate the cell layer and incorporate into the cells. As a result, the biologically responsive compound can denature the cells into which it is incorporated, thus reducing inflammatory cell activation leading to the inhibition of the smooth muscle cell proliferation. Consequently, restenosis can be inhibited. If the coating also contains a drug, additional therapeutic effect can be achieved. The low molecular weight salts (NaCl, KCl), if used, can also penetrate the cells of the tissue at the diseased site and destroy the restenosis cells by altering local environmental properties.

Poly(ethylene-co-vinyl alcohol) (EVAL®) is one example of a polymer that can be used to fabricate the matrix layer, the optional primer layer, the optional topcoat, and/or optional finishing layer. EVAL has the general formula $-[CH_2-CH_2]_m-[CH_2-CH(OH)]_n-$. EVAL is a product of hydrolysis of ethylene-vinyl acetate copolymers and may also be a terpolymer including up to 5 molar % units derived from styrene, propylene and other suitable unsaturated monomers. A brand of copolymer of ethylene and vinyl alcohol distributed commercially under the trade name EVAL by Aldrich Chemical Co. of Milwaukee, Wis., and manufactured by EVAL Company of America of Lisle, Ill., can be used. Other suitable polymers can also be used to form the matrix layer, the optional primer layer, the optional topcoat, and/or optional finishing layer. Representative examples include poly(hydroxyvalerate), poly(L-lactic acid), polycaprolactone, poly(lactide-co-glycolide), poly(hydroxybutyrate), poly(hydroxybutyrate-co-valerate), polydioxanone, poly-orthoester, polyanhydride, poly(glycolic acid), poly(D,L-lactic acid), poly(glycolic acid-co-trimethylene carbonate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

The polymer can be applied to the stent by dissolving the polymer in a solvent and applying the resulting solution on the stent by any suitable method, for example, by spraying or dipping. Representative examples of some suitable solvents include N,N-dimethylacetamide (DMAC), N,N-dimethylformamide (DMFA), tethrahydrofurane (THF), or dimethylsulphoxide (DMSO).

The biologically responsive compounds to be incorporated in the matrix layer, the topcoat, and/or the finishing layer can be polymeric, oligomeric or low-molecular weight compounds. Examples of suitable biologically responsive compounds include poly(ethylene glycol) (PEG), PLURONIC polyols, poly(vinyl pyrrolidone), hyaluronic acid, carboxymethylcellulose, poly(ethylene imine), poly(vinyl alcohol), polyacrylamide, sulfonated dextrane, silk-elastin block-co-polymers, poly(ethylene oxide-co-ethylene imine), poly(ethylene oxide-co-vinyl pyrrolidone), poly(ethylene oxide-co-vinyl alcohol), poly(ethylene oxide-co-acrylamide), poly(ethylene oxide-co-sulfonated dextrane), PEG-hyaluronic acid adducts, adducts of silk-elastin block-copolymers with hyaluronic acid, sodium dodecyl sulfate (SDS), and physical blends thereof.

PEG is a biologically compatible polyglycol product having the general formula $H[-O-CH_2-CH_2-]_nOH$. PEG can be in an oligomeric or polymeric form and can have a molecular weight within a range of between about 500 and about 30,000 Daltons, for example, 10,000 Daltons.

PLURONIC polyols are also biologically compatible oligomeric or polymeric substances which are various brands of poly(ethylene oxide-co-propylene oxide) having the general formula $HO[-CH_2-CH_2-O-]_x[CH_2-CH_2-CH_2-O-]_y[-CH_2-CH_2-O-]_xH$. PLURONIC polyols are manufactured by BASF Corp. of Parsippany, N.J. and can have a molecular weight within a range of between about 950 and about 4,000 Daltons, typically, between about 1,750 and about 3,500 Daltons. "x" and "y" in the formula of PLURONIC shown above are integers selected in such a way that the terminal hydrophilic fragments (the "x" units) comprise between about 50 and about 70% (by mass) of the compound.

Hyaluronic acid is a linear polysaccharide composed of disaccharide units of N-acetylglucosamine and D-glucoronic acid, having a relatively high molecular weight. Silk-elastin protein block-copolymers combine the repeating blocks of amino acids thus providing the copolymer with the mechanical strength characterizing silk and the flexibility characterizing elastin. Silk-elastin block-copolymer can be obtained from Protein Polymer Technologies, Inc. of San Diego, Calif.

A drug or a combination of drugs can be incorporated into the stent coating. The drug can include any therapeutic substance capable of exerting a therapeutic or prophylactic effect in the practice of the present invention. For example, the drug could be designed to inhibit the activity of vascular smooth muscle cells. It can be directed at inhibiting abnormal or inappropriate migration and/or proliferation of smooth muscle cells to inhibit restenosis. The drug may include small molecule drugs, peptides or proteins. Examples of drugs include antiproliferative substances such as actinomycin D, or derivatives and analogs thereof (manufactured by Sigma-Aldrich of Milwaukee, Wis., or COSMEGEN™ available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co. of Stamford, Conn.), docetaxel (e.g. Taxotere®, from Aventis S.A. of Frankfurt, Germany) methotrexate, azathioprine, vincristine, vinblastine, fluorouracil, doxorubicin hydrochloride (e.g. Adriamycin® from Pharmacia & Upjohn of Peapack, N.J.), and mitomycin (e.g. Mutamycin® from Bristol-Myers Squibb). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (bivalirudin, Biogen, Inc. of Cambridge, Mass.). Examples of such cytostatic or antiproliferative agents include angiopeptin, angiotensin converting enzyme inhibitors such as captopril (e.g. Capoten® and Capozide® from Bristol-Myers Squibb), cilazapril or lisinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by name of everolimus, available from Novartis of New York, N.Y.), 40-O-(3-hydroxy)propyl-rapamycin, 40-O-[2-(2-hydroxy)ethoxy]ethyl-rapamycin, and 40-O-tetrazole-rapamycin.

The coating of the present invention has been described in conjunction with a stent. However, the coating can also be used with a variety of other implantable medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, coronary shunts and endocardial leads (e.g., FINELINE® and ENDOTAK®, available from Guidant Corporation). The underlying structure of the device can be of virtually any design. The device can be made of a metallic material or an alloy such as, but not limited to, cobalt-chromium alloys (e.g., ELGILOY®), stainless steel (316L), "MP35N," "MP20N," ELASTINITE® (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

EXAMPLES

Embodiments of the present invention can be illustrated by the following Examples.

Example 1

A composition can be prepared by mixing the following components:
(a) between about 0.1 mass % and about 15 mass %, for example, about 1.2 mass % of EVAL;
(b) between about 0.05 mass % and about 1.0 mass %, for example, about 0.5 mass % of PEG;
(c) between about 0.05 mass % and about 1.0 mass %, for example, about 0.075 mass % of poly(vinyl pyrrolidone); and
(d) the balance, DMAC solvent.

The composition is applied onto the stent and dried. The composition can be applied onto the stent by any conventional method known to those with ordinary skill in the art, for example, by spraying or dipping. A primer (e.g., made from essentially 100% EVAL) can be optionally applied on the surface of the bare stent. For a stent having a length of 13 mm and diameter of 3 mm, the total amount of solids of the matrix layer can be about 300 micrograms (corresponding to the thickness of between about 15 and 20 microns). "Solids" means the amount of the dry residue deposited on the stent after all volatile organic compounds (e.g., the solvent) have been removed.

A composition comprising between about 0.1 mass % and about 15 mass %, for example, about 2.0 mass % of EVAL and the balance of DMAC, can be applied onto the dried matrix layer and dried, to form a topcoat layer. The topcoat layer can be applied by any conventional method mentioned above and can have, for example, a total solids weight of about 200 µg.

Example 2

A composition can be prepared by mixing the following components:
(a) between about 0.1 mass % and about 15 mass %, for example, about 2.0 mass % of EVAL;
(b) between about 0.05 mass % and about 1.0 mass %, for example, about 0.7 mass % of EVEROLIMUS; and
(c) the balance, DMAC solvent.

The composition can be applied onto a stent by any conventional method as described in Example 1, to form a matrix layer with about 200 µg of total solids.

A composition comprising between about 0.1 mass % and about 15 mass %, for example, about 2.0 mass % of EVAL and the balance of DMAC can be applied onto the dried matrix layer to form a topcoat layer. The topcoat can have, for example, a total solids weight of about 300 µg.

Following the formation of the topcoat, a composition comprising between about 0.1 mass % and about 10 mass %, for example, about 1.3 mass % of EVAL, between about 0.1 mass % and about 1.5 mass %, for example, about 0.7 mass % of PEG and the balance of DMAC, can be applied onto the dried topcoat to form a finishing coat. The finishing coat can have, for example, a total solids weight of about 200 µg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device, comprising at least one polymer and a biologically responsive component physically blended with the polymer, wherein the biologically responsive component is selected from the group consisting of poly(ethylene imine), polyacrylamide, sulfonated dextran, silk-elastin block-copolymers, poly(ethylene oxide-co-ethylene imine), poly(ethylene oxide-co-vinyl pyrrolidone), poly(ethylene oxide-co-vinyl alcohol), poly(ethylene oxide-co-acrylamide), poly(ethylene oxide-co-sulfonated dextran), PEG-hyaluronic acid adducts, adducts of silk-elastin block-copolymers with hyaluronic acid, sodium dodecyl sulfate, and blends thereof.

2. The coating of claim 1, wherein the implantable medical device is a stent.

3. The coating of claim 1, further comprising a therapeutic substance.

4. The coating of claim 3, wherein the therapeutic substance is selected from the group consisting of estradiol, paclitaxel, heparin, heparin derivatives containing hydrophobic counter-ions, docetaxel, rapamycin, and derivatives thereof, and combinations thereof.

5. The coating of claim 1, wherein the at least one polymer is poly(ethylene-co-vinyl alcohol).

6. The coating of claim 1, further comprising a low molecular weight salt.

7. The coating of claim 6, wherein the low molecular weight salt is sodium chloride and/or potassium chloride.

8. The coating of claim 1, further comprising poly(ethylene glycol) physically blended with the biologically responsive component.

9. The coating of claim 8, wherein the poly(ethylene glycol) physically blended with the biologically responsive component has a molecular weight of between about 8,000 and about 30,000 Daltons.

10. A method for inhibiting restenosis, the method comprising delivering a restenosis-inhibiting substance to a treatment site in a patient, the restenosis-inhibiting substance physically blended into a polymeric coating according to claim 1, the polymeric coating having been applied on an implantable medical device, wherein delivering the restenosis-inhibiting substance comprises implanting the coated implantable medical device in the patient at the treatment site.

11. The method of claim 10, wherein the implantable medical device is a stent.

12. The method of claim 10, wherein the polymeric coating further comprises a therapeutic substance.

13. The method of claim 10, wherein the polymeric coating further comprises a low-molecular weight salt.

14. The method of claim 13, wherein the low molecular weight salt is sodium chloride and/or potassium chloride.

15. The method of claim 10, wherein the polymeric coating further comprises poly(ethylene glycol) physically blended with the biologically responsive component.

16. The method of claim 15, wherein the poly(ethylene glycol) physically blended with the biologically responsive component has a molecular weight of between about 8,000 and about 30,000 Daltons.

17. A method of forming a coating according to claim 1 on an implantable medical device, the method comprising:
applying the physical blend of the polymer and the biologically responsive component to an implantable medical device.

18. The method of claim 17, wherein the physical blend further comprises poly(ethylene glycol) physically blended with the biologically responsive component.

19. The method of claim 18, wherein the poly(ethylene glycol) physically blended with the biologically responsive component has a molecular weight of between about 8,000 and about 30,000 Daltons.

20. The method of claim 17, wherein the implantable medical device is a stent.

* * * * *